US005637768A

United States Patent [19]

Jund et al.

[11] Patent Number: 5,637,768

[45] Date of Patent: Jun. 10, 1997

[54] PROCESS FOR MAKING (2S,5S)-5-FLUOROMETHYLORNITHINE

[75] Inventors: Karin Jund, Strasbourg; Jean-Bernard Ducep, Sundhoffen, both of France

[73] Assignee: Merrell Pharmaceuticals, Inc., Cincinnati, Ohio

[21] Appl. No.: 491,968

[22] PCT Filed: Nov. 19, 1993

[86] PCT No.: PCT/US93/11283

§ 371 Date: Jul. 18, 1995

§ 102(e) Date: Jul. 18, 1995

[87] PCT Pub. No.: WO94/17795

PCT Pub. Date: Aug. 18, 1994

[30] Foreign Application Priority Data

Feb. 5, 1993 [FR] France .................................. 93 400303

[51] Int. Cl.$^{6}$ .................................................. C07C 229/00

[52] U.S. Cl. ............................................................ 562/561

[58] Field of Search ............................ 514/564; 562/561

[56] References Cited

FOREIGN PATENT DOCUMENTS 10326766 8/1989 European Pat. Off. .

OTHER PUBLICATIONS

Biosis Abs. #95042852, Sano et al., Arch. Neurol. 49(11) 1992 pp. 1137–1141.

Neuroscience Letters vol. 117, pp. 358–362 (1990) Siegried Hoyer et al. "Ammonia is endogenously generated in the brain in the presence of presumed and verified d type".

Clinical Neuropathology vol. 7, No. 1, pp. 10–15 (1988) C.L. Dolman et al. "Servere cerebal damage in ornithin transcarbamylase deficiency".

Gastroenterology vol. 67, No. 3, pp. 347–374 (1974) Y. Edward Hsia "Inherited hyperammonemic syndromes".

Neurochemical Reserach vol. 18, No. 3, pp. 235–245 (1993) Nikolaus Seiler "Is ammonia a pathogenetic factor in Alzheimer's disease?".

Pharmacol. Toxicol. vol. 72, No. 2, pp. 116–123 (1993) Nikolaus Seiler et al. "Enhanced endogenos ornithine concentrations protect against tonic seizures and coma in acute ammonia intoxication".

Life Sciences vol. 45, No. 11, pp. 1009–1019 (1989) Nikolaus Seiler et al. "Ornithine aminotransferase activity, liver ornithine concentration and acute ammonia intoxication".

Biochem. J. vol. 268, No. 2, pp. 409–414 (1990) Frank Bolkenius et al. "DL–Canaline and 5–fluoromethylornithine".

Biochem. J. vol.253, pp. 481–488 (1988)–G. Daune et al. "5–Fluoromethylornithine, an Irreversible and Specific Inhibitor of L–Ornithine: 2–Oxo–Acid Aminotransferase".

*Primary Examiner*—Raymond Henley, III
*Attorney, Agent, or Firm*—Carolyn D. Moon

[57] ABSTRACT

The present invention is directed to a process for making (2S,5S)-5-fluoromethylornithine through the reaction of wet penicillin acylase with (2R,5R) and (2S,5S)-6-fluoromethyl-3-(phenylactyl)-amino-2-piperidone and the addition of an acid to the resulting product.

1 Claim, No Drawings

PROCESS FOR MAKING (2S,5S)-5-FLUOROMETHYLORNITHINE

This application is a 371 of PCT/US93/11283 filed Nov. 19, 1993.

The present invention comprises the use of certain inhibitors of ornithine aminotransferase, and more preferably, certain 5-substituted ornithine derivatives for the treatment of dementia of the Alzheimer's type (DAT) alone and in combination with other agents.

BACKGROUND OF THE INVENTION

The ammonium ion ($NH_4$+) serves a major role in the maintenance of acid-base balance, but is toxic in high concentrations. By the body it is produced from many precursors (nucleic acids, proteins, amino acids, hexosamines, primary amines) by different reactions, and introduced into the body by exogenous sources such as the break down of dietary proteins by intestinal bacteria.

About 20% of the urea [$CO(NH_2)_2$] produced in the body diffuses into the gut where it is converted by bacteria to ammonia and carbon dioxide. The ammonia is absorbed and converted back to urea in the liver by way of the ornithine (urea) cycle, the major pathway for elimination of ammonia. Thus, acute and chronic diseases of the liver impair the ability of the liver to remove ammonia from the body.

Elevated levels of ammonia can easily pass the blood brain barrier causing encephalopathies (degenerative diseases of the brain). One cause of neurogenic encephalopathy is bacterial infections of the urinary tract (e.g. the neurogenic bladder). Another cause is deficient detoxification of ammonia due to acute or chronic liver disease which leads to hepatogenic encephalopathy. An important factor in the pathogenesis of this disease has been identified as exogenous (gastrointestinal) ammonia.

Proteins, nucleic acids, amino acids and hexosamines have long been suggested as other sources of cerebral ammonia. Oxidative deaminations of primary amines (monoamines, diamines and polyamines), glycine catabolism via the glycine cleavage system, deaminations of purines and pyrimidines and glucosamine-6-phosphate, among others, are well known ammonia generating reactions, which may contribute to the steady-state level of brain ammonia.

Dementia of the Alzheimer's Type (DAT) is another type of degenerative brain disease with unknown etiology (although several hypotheses have been postulated). There have been recent reports of not only elevated concentrations of ammonia in the brain of DAT patients, but also reports that ammonia is endogenously generated in excess therein. Hoyer, S., et al., *Neurosci. Lett.* 117:358–362 (1990). There were two reports that arterial ammonia levels were significantly higher in DAT patients than in appropriately matched control subjects. Fisman, M., et al., *Am. J. Psychiatry* 142:71–73 (1985); Fisman, M., et al., *J. Am. Ger. Soc.* 37:1102 (1989). Patients who met the diagnostic criteria of DAT, but had no liver disease, nor urinary tract infections had levels of 208±136 μg ammonia per 100 ml of plasma. The normal range was 20–94 μg/100 ml; 83% of the patients had blood ammonia concentrations above the normal limits. Branconnier, R. J., et al., *Am. J. Psychiatry* 143: 1313 (1986). Arterio-venous differences of ammonia in patients suffering from advanced DAT, and in patients clinically diagnosed as having incipient dementia, in all probability DAT of early onset, were reported. Healthy volunteers showed an average ammonia uptake by the brain of 72±7 $\mu g.kg^{-1}.min.^{-1}$. In striking contrast, 27±3 $\mu g.kg^{-1}.min.^{-1}$ of ammonia was released from the brains of patients with advanced DAT. Patients with presumed early-onset DAT released 256±162 $\mu g.kg^{-1}.min.^{-1}$ ammonia into the circulation. These findings suggest excessive ammonia production within the brain, with or without a deficient mechanism of ammonia detoxification. Hoyer, S., et al. *Neurosci. Lett.* 117:358–368 (1990).

The present invention recognizes hyperammonemia as an important factor in at least the symptomatology and progression of DAT. As further described hereafter, cerebral hyperammonemia may influence those factors which are considered to be hallmarks of DAT.

CEREBRAL HYPERAMMONEMIA AND DAT a) SYNAPTIC TRANSMISSION IN AMMONIA INTOXICATION

Ammonia is capable of interfering with the function of the major excitatory (glutamatergic) and the major inhibitory (GABAergic) neuronal systems of the vertebrate central nervous system which is impaired in the patient having DAT.

Based on experimental results it was calculated that an increase of ammonia to about 0.5 $\mu mol.g^{-1}$ brain i.e. a 2–5-fold increase, is sufficient to disturb excitatory and inhibitory synaptic transmission and to initiate the encephalopathy related to acute ammonia intoxication Raabe, W., *Neurochem. Pathol.* 6: 145–166 (1987). Thus, it seems evident that slowly progressing pathogenic mechanisms may be initiated even at brain ammonia concentrations only slightly above physiological levels.

Glutamate-mediated excitatory synaptic transmission is decreased by ammonia. Whether this effect is related to a depletion of glutamate in presynaptic terminals is unclear at present.

Inhibitory synaptic transmission is also decreased by ammonia, by hyperpolarizing $Cl^-$-dependent inhibitory (e.g. GABAergic) neurons. This effect is related to the inactivation of the extrusion of $Cl^-$ from neurons by ammonia. By the same action ammonia also decreases the hyperpolarizing action of $Ca^{2+}$- and voltage dependent $Cl^-$-currents. Since a large proportion of the GABAergic and other inhibitory neurons control inhibitory inputs, ammonia produces an increase in neuronal excitation by "disinhibition".

b) REDUCED GLUCOSE UTILIZATION

Most conspicuous findings of experimental and human diseases with hyperammonemic states, namely the impairment of brain glucose utilization, with concomitantly decreased rates of energy metabolism and astrocytic alterations, characterized as "Alzheimer type II gliosis" are characteristic for DAT brains as well: in PET (positron emission tomography) studies cerebral glucose utilization was found to be predominantly reduced in the parieto-temporal cortex. Overall cerebral glucose utilization was found to be diminished by about 50% with normal oxygen consumption in early-onset, but reduced oxygen consumption in late onset DAT. The impairment of brain energy metabolism in DAT, and of enzymes involved in energy metabolism, has subsequently been reported by several investigators.

c) INTERFERENCE WITH GLIA FUNCTION

Astrocyte abnormalities are a characteristic of DAT. Observations supporting the idea that reactive astrocytes may mediate neuropathologic events of DAT, including the facilitation of extracellular depositions of β-amyloid protein have been reported. Frederickson, *Neurobiol. Aging* 13:239–253 (1992).

Astrocytic damage by ammonia is followed by a decrease of glutamine synthetase activity, as was evidenced from the reduction of the activity of this enzyme by 15% in rats with portacaval shunts, Butterworth, R. F., et al., *J. Neurochem.* 51:486–490 (1988). However, this decrease in synthetase activity may cause further damage to astrocytes. It is well established that glutamine synthetase is critically involved in the regulation of intracellular ammonia and acid-base balance. Any derangement of the function of this enzyme will be followed by the amplification of ammonia toxicity. Therefore, it is not surprising that an increased intracellular pH, and swelling of astrocytes was observed in hyperammonemic rats, Swain, M. S., et al. *Am. J. Physiol.* 261:R1491–51496 (1991).

Increasing evidence emerges for a role of microglia in DAT pathology McGeer, P. L., et al. *Can. J. Neurol. Sci.* 18: 376–379 (1991). These cells are seen in many degenerating cells, and virtually every senile plaque has microglial cells or cell processes in the plaque. It is believed that microglia invasion is an indication for the brain's attempt to rid itself of cell debris. Since β-amyloid precursor protein is likely to be formed in microglia these cells may contribute to the formation of β-amyloid protein depositions in two ways, by phagocytosis of nerve ending membranes, and by their intrinsic β-amyloid precursor protein.

d) HYPERAMMONEMIA AND EXCITOTOXIC AMINO ACIDS

Presumably the most conspicuous difference between the amino acid patterns of cirrhotic and DAT patients is the several-fold increase of glutamine in all brain regions of cirrhotics, but no change in the concentration of this amino acid in the brains of DAT patients. Likewise, no increase of glutamine was detected in the cerebrospinal fluid (CSF) of patients with DAT, whereas the levels of this amino acid were elevated in the CSF of experimental animals with portal-systemic encephalopathy. These findings suggest the inability of the brains of DAT patients to enhance glutamine formation above a certain level and may be taken as an indication for a considerable sensitivity of DAT brains even to small increases in the rate of ammonia formation. Due to the elevation of ammonia levels, reductive amination of 2-oxoglutarate (catalyzed by glutamate dehydrogenase) may take place, both in DAT and hepatogenic encephalopathy. Presumably, this "extra" glutamate can only be removed from the brain as glutamine in the latter disease not in DAT brains, due to its limited glutamine synthetase activity. Glutamate formation from 2-oxoglutarate impairs at the same time energy metabolism, by decreasing the equilibrium concentration of this substrate of the tricarboxylic acid cycle.

Glutamate concentrations are lower in the brains of DAT patients than in age-matched controls, due to losses of glutamatergic neurons, but CSF levels of glutamate are elevated, both in DAT, Pomara, N., et al. *Am. J. Psychiatry* 149: 251–254 (1992), and in portal systemic encephalopathy Therrien, G., et al., *Metabolic Brain Dis.* 6:65–74 (1991), indicating enhanced extracellular concentrations of this amino acid. Disregarding the mentioned possibility of the enhanced formation of glutamate by reductive amination of 2-oxoglutarate the increase of extracellular glutamate concentrations is most probably a result of the impairment of the uptake of glutamate into perineuronal astrocytes due to the deranged astrocyte function by ammonia. Since it is well established that the neurotoxic effects of glutamate are enhanced by inhibition of uptake sites, derangement of glial uptake mechanisms could be a major reason for excitotoxic cell damage in DAT.

The release of aspartate from the brains of patients with early-onset DAT is indicative for a further cause of excitotoxic damage during a certain stage of the disease. Patients with a mean age of 60 years had normal CSF levels of aspartate. Pomara, N., et al., *Am. J. Psychiatry* 149: 251–254 (1992).

There is evidence for the selective loss of glutamate receptors in cortex and hippocampus of DAT brains. In the cerebellum of hyperammonemic rats a decrease of the number of both high- and low-affinity binding sites of glutamate was noticed. The decrease was only in the N-methyl-D-aspartate-specific binding sites, without any alterations in the binding sites of kainate or quisqualate. These effects were mimicked when the membrane preparations from normal animals were incubated with ammonium acetate. Binding of muscimol (a GABA receptor agonist) was enhanced under the same experimental conditions Raghavendra Rao, V. L., et al. *Neurosci. Lett.* 130:251–254 (1991). These observations show again the ability of ammonia to affect functions of both glutamatergic and GABAergic neurons.

The compounds of the present invention have been described in European Patent application number 88400275.9 filed Feb. 5, 1988, publication number 0 326 766 entitled 5-Substituted Ornithine Derivatives, which is hereby incorporated herein. These compounds were disclosed therein to be effective in treating conditional deficiencies of ornithine and in cases of ammonia intoxication.

Ornithine is a substrate in the urea cycle. The urea cycle is effective in incorporating ammonium ions into urea in order to be eliminated from the body. The compounds of the present invention inactivate ornithine: 2-oxoacid aminotransferase (OAT). It is believed that by enhancing the level of tissue ornithine concentrations due to inactivation of OAT over an extended period of time, urea formation in the liver and presumably in some other tissues would be a consequence thereof, thereby lowering blood and cerebrospinal fluid ammonia concentrations. These compounds are useful in numerous well known human illnesses associated with elevated blood and cerebrospinal fluid ammonia concentrations, among which, for example, are liver cirrhosis, fulminant hepatic failure and urinary tract/bladder infections.

Despite the foregoing, DAT has not previously been thought of as a condition benefited by the lowering of ammonia levels. Indeed, the use of OAT inhibitors presents an especially effective method of treatment for DAT since most Alzheimer patients usually have normal liver function. Thus the use of the compounds of the present invention present a much needed new approach to the treatment of DAT.

It is an object of the present invention to provide a new use for the compounds of the present invention by treating DAT. It is another object of the present invention to provide a synthesis for an enantiomer of the compounds of the present invention and yet another objective is to present combination therapy useful in the treatment of DAT.

SUMMARY OF THE PRESENT INVENTION

The present invention comprises the new use for the treatment of DAT with OAT inactivators, preferably substituted ornithine derivatives and more preferably 5-substituted ornithine derivatives of the formula:

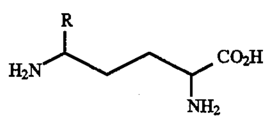

wherein R is a —$CH_2F$, $CHF_2$, —CHClF, —C≡CH, CH=$CH_2$ or CH=C=$CH_2$ group, stereoisomer, or a pharmaceutically acceptable acid addition salt thereof. The treatment of DAT may be a combination therapy comprising administration of OAT inhibitors and other agents useful in lowering brain ammonia levels in the patient.

DETAILED DESCRIPTION OF THE PRESENT INVENTION

As used herein "DAT" or "dementia of the Alzheimer's type" means progressively deteriorating organic mental syndromes in which there is impairment in short-term and long-term memory. This degenerative dementia can be mild (impairment of work or social activities but able to live alone), moderate (some degree of supervision needed) or severe (continual supervision required).

Impairment in short-term memory is the inability to learn new information and may be demonstrated by, for example, the patients' inability to remember three objects after five minutes. Long-term memory impairment is the inability to remember information that was known in the past and may be indicated by, for example, the patients' inability to remember past personal information such as their birthplace, occupation, what happened yesterday, etc., or the inability to remember facts of common knowledge. There is typically impairment in abstract thinking, impairment in judgment, personality changes or other disturbances of higher cortical functions.

"Patient" as used herein means warm-blooded animals, such as for example rats, mice, dogs, cats, guinea pigs, primates and humans. The term "treat", or forms thereof, means to prevent or alleviate the patient's disease or condition.

The term "stereoisomer" is a general term for all isomers of individual molecules that differ only in the orientation of their atoms in space. It includes mirror image isomers (enantiomers), geometric (cis/trans) isomers, and isomers of compound with more than one chiral center that are not mirror images of one another (diastereoisomers). In the present invention, racemic mixtures of compounds of formula I may have four enantiomers and only one of the four enantiomers may be preferred over the others.

The term "combination therapy" can mean concurrent or consecutive administration of two or more agents. For example, concurrent administration can mean one dosage form in which the two or more agents are contained whereas consecutive administration can mean separate dosage forms administered to the patient at different times and maybe even by different routes of administration.

Any agent may be used in combination therapy with the compounds of the present invention which are useful in treating DAT. Preferably agents useful in lowering ammonia levels in the brain of DAT patients are used. For example, agents useful in promoting the excretion of ammonia through the urea cycle such as ornithine, citrulline and arginine may be used. Preferably, agents which are believed to lower brain ammonia levels independent of the urea cycle are used such as L-acetylcarnitine and L-carnitine.

As in most inventions, there are preferred embodiments. In the present invention it is preferred that R is $CH_2F$ (Example 1 in EP 326 766), and most preferably, one of its enantiomers which is believed to be (S/S)-2,5-diamino-6-fluoro-hexanoic acid.

EXAMPLE 1

2,5-Diamino-6-fluoro-hexanoic acid is obtained as described in European patent 326 766. The enantiomers are separated using any appropriate method such as HPLC, or alternative methods may be used as follows, Asymmetric synthesis of (2S,5S)-6-fluoro-2,5-diaminohexanoic acid, dihydrochloride

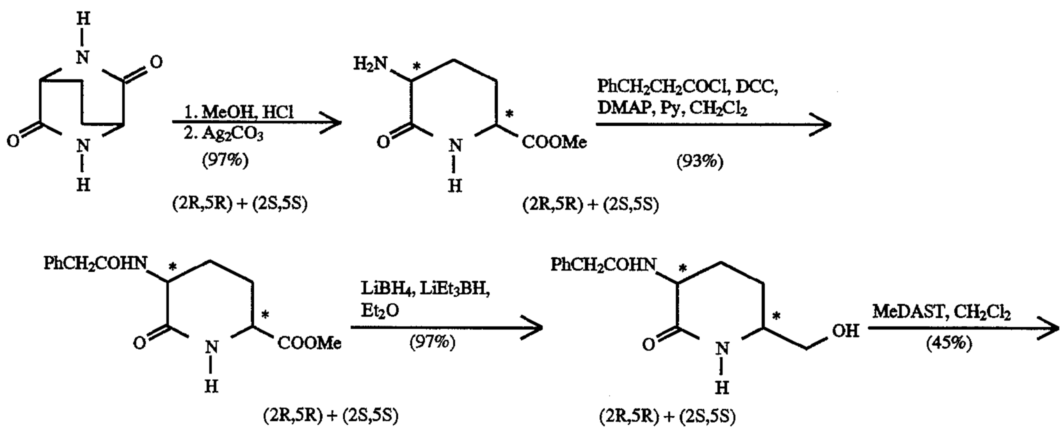

-continued

Asymmetric synthesis of (2S,5S)-6-fluoro-2,5-diaminohexanoic acid, dihydrochloride

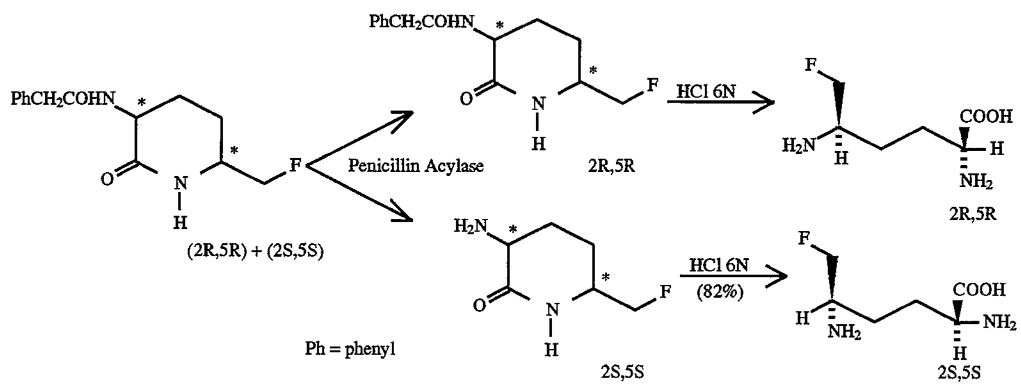

(2R, 5R) and (2S,5S) -Methyl-3-amino-2-piperidone-6-carboxylate 2,5-Diazabicyclo (2.2.2) octane-3,6-dione [*J. Med. Chem.* 1974, 17, 481–487, P. A. Sturm, D. W. Henry, Antifilarial agents. Diazabicyclooctanes and Diazabicycloheptanes as bridged analogs of diethyl carbamazine] (10.75 g, 0.0768 mol) is dissolved in a solution of hydrochloric acid in anhydrous methyl alcohol (560 ml, 0.27 M). The mixture is stirred at 20° C. for 18 hours, then neutralized with silver carbonate (21.5 g, 0.082 mol) and filtered over a celite pad. The solvent is evaporated and the residue is dried overnight. The title compound is obtained as a white solid (12.8 g, 97% yield).

$^1$H NMR (360 MHz, $CD_3OD$) δ ppm: 3.85 (m, 1H, CHCOO); 3.55 ,(m, 1H, $CHNH_2$); 3.40 (s, 3H, $CH_3$); 1.9 and 1.4 (2m, 2×2H $CH_2CH_2$).

MS: monoTFA derivatives: m/e=269 ($MH^+$); 286 ($MNH_4^+$) Chiral GC: 145° C., 1 bar $H_2$, TFA derivatives. 2 peaks: 15.63 min and 16.64 min.

(2R, 5R) and (2S,5S)-Methyl-3-(phenylacetyl) amino-2-piperidone-6-carboxylate

To a mixture of phenylacetic acid (10.2 g, 0.075 mol), dicyclohexyl carbodiimide (13.5 g, 0.075 mol), pyridine (7.2 ml, 0.061 mol) and 4-dimethylaminopyridine (0.9 g, 0.0073 mol) in anhydrous dichloromethane (400 ml), is added (2R,5R) and (2S,5S)-methyl-3-amino-2-piperidone-6-carboxylate (12.8 g, 0.0744 mol). The reaction mixture is stirred at 20° C. for 24 hours, then the dicyclohexylurea formed is filtered off and the filtrate is evaporated. The residue is purified by flash chromatography on silica using methyl alcohol/ethyl acetate 5/95 as eluent. The title compound is obtained as a white solid (19.61 g, 93% yield).

$^1$H NMR (200 MHz, $CD_3OD$) δ ppm: 7.87 (m, 5H, Ph); 6.55 (d, 1H, NH); 6.40 (s, 1H, NH-1); 4.35 (m, 1H, H-3); 4.12 (m, 1H, H-6); 3.77 (s, 3H, COOMe); 3.54 (s, 2H, $COCH_2Ph$); 2.5 (m, 1H, H-4A); 2.2 (m, 2H, H-5); 1.5 (m, 1H, H-4B).

HPLC: Chiralpak AD, 250×4.6 mm, 21° C., EtOH/MeOH/heptane: 25/45/30, 1 ml/min, 210 nm, 2 peaks: 7.26 min and 12.51 min.

Analysis calculated for $C_{15}H_{18}N_2O_4$ (290.31): C, 62.06; H, 6.25; N, 9.65. Found: C, 62.50; H, 6.26; N, 9.73. m.p. 138° C.

(2R,5R) and (2S,5S)-3-(Phenylacetyl)amino-2-piperidone-6-methylalcohol

To a slurry of (2R,5R) and (2S,5S)-methyl-3-(phenylacetyl)amino-2-piperidone-6-carboxylate (1.451 g, 0.005 mol) in anhydrous diethyl ether (50 ml) and tetrahydrofuran (12.5 ml) is added lithium borohydride (0.109 ml, 0.005 mol) and lithium-tri-sec-butylborohydride (0.5 ml, 1M, 0.0005 mol). The reaction mixture is refluxed for 12 hours, then methyl alcohol is added (5 ml) and the solvents are evaporated. The residue is purified by flash chromatography on silica gel using methyl alcohol/ethyl acetate (8/92) as eluent. After recrystallization, the title compound is obtained as a white solid (2.275 g, 97% yield).

$^1$H NMR (200 MHz, $CD_3OD$) δ ppm: 7.7 (m, 5H, ph); 4.05 (m, 1H, H-3); 3.25 (m, 3H, $CHCH_2O$); 1.55 (m, 4H, H-4, H-5).

HPLC: Chiralpak AD, 250×4.6 mm, 21° C., EtOH/heptane: 60/40, 1ml/min, 210 nm 2 peaks: 5.37 min and 6.48 min.

Analysis calculated for $C_{14}H_{18}N_2O_2$ (262.311): C, 64.11; H, 6.92; N, 10.68. Found: C, 64.12; H, 6.86; N, 10.68. m.p. 158° C.

(2R,5R) and (2S ,5S)-6-Fluoromethyl-3-(phenylacetyl)amino-2-piperidone

A suspension of (2R,5R) and (2S,5S)-3-(phenylacetyl)-amino-2-piperidone-6-methylalcohol (52.4 mg, 0.2 mmol) in 5 ml anhydrous dichloromethane is cooled to −78° C. Dimethylaminosulfurtrifluoride (53.2 mg, 0.4 ml, 0.4 mmol) is added slowly to the mixture. After 5 minutes at −78° C., the reaction mixture is allowed to reach room temperature, and stirred for another 16 hours. The reaction is quenched with icy water. The organic phase is diluted with dichloromethane (25 ml) and washed with water. The organic phase is dried over sodium sulfate, filtered and the solvents are evaporated. The residue is purified by flash chromatography on neutral aluminum oxyde activity III using methyl alcohol/ethyl acetate: 8/92 as eluent. After recrystallization in chloroform/pentane the title compound is obtained as white crystals (0.024 g, 45% yield).

$^1$H NMR (360 MHz, $CD_3OD$) δ ppm: 7.3 (m, 5H, $C_6H_5$); 6.47 (d, 1H, $NHCOCH_2Ph$); 6.27 (s, 1H, NH); 4.35 (dAB, $H_A$, $JH_AF$=46.4 Hz) 4.33 (dAB, 1H, $JH_BF$=47.33 Hz); 4.24 (m, 1H, H-3); 3.75 (m, 1H, H-6); 3.6 (s, 2H, $CH_2Ph$); 2.42 (m, 1H, $H_2$).

$^{19}$F NMR (338.8 MHz, $CHCl_3$) δ ppm: −62.82 (dt, JHF=46.8 Hz). HPLC Chiralpak AD, 250×4.6 mm, 21° C., EtOH/heptane: 60/40, 0.5 ml/min, 210 nm. 2 peaks: 12.8 min and 14.8 min.

Analysis calculated for $C_{14}H_{17}N_2O_2F$ (264.30): C, 63.62; H, 6.48; N, 10.60. Found: C, 63.17; H, 6.56; N, 10.52.

(2R, 5R) and (2S,5S)-6-Fluoromethyl-3-(phenylacetyl)amino-2-piperidone and (2S,5S)-6-Fluoromethyl-3-amino-2-piperidone To a solution of (2R,5R) and (2S,5S)-6-fluoromethyl-3-(phenylacetyl)-amino-2-piperidone (0.097 g, 0.37 mmol) in phosphate buffer pH 7.0 (11 ml, 0.1M) is added wet penicillin acylase (0.040 g). After stirring for 30 minutes, the enzyme is filtered out, the solution is washed with dichloromethane to remove the (2R,5R)-6-fluoromethyl-3-(phenylacetyl)-amino-2-piperidone (0.057 g). Evaporation of the aqueous phase affords the (2S,5S)-6-fluoromethyl-3-amino-2-piperidone as a white solid (0.023 g).

HPLC: Chiralpak AD, 250×4.6 mm, 21° C., EtOH/heptane: 60/40; 0.5 ml/min, 210 nm. 1 peak: 14.8 min.

(2S,5S)-6-Fluoro-2,5-diaminohexanoic acid, dihydrochloride, and ((2S,5S)-5-fluoromethylornithine, dihydrochloride)

A solution of (2S,5S)-6-fluoromethyl-3-amino-2-piperidone (0.020 g, 0.17 mmol) in hydrochloric acid (1 ml, 6N) is refluxed for 2.5 hours. The solution is diluted with water (2 ml) and washed 4 times with dichloromethane (4 ml), the aqueous phase is evaporated and the residue is recrystallized in methyl alcohol/diethyl ether. The title compound is obtained as white crystals (15 mg, 82% yield).

$^1$H NMR (360 MHz, $CD_3OD$) δ ppm: 4.4 (m, 2H, $CH_2F$); 3.8 (m, 1H, H-2); 3.3 (m, 1H, H-5); 1.7 (m, 4H, $CH_2CH_2$).

$^{19}$F NMR (338.8 MHz, $CHCl_3$) δ ppm: −69.15 (dt, $^3J$=23 Hz, $^2J$=47 Hz).

EXAMPLE 2

In order to test the efficacy of treatment with the compounds of the present invention, blood ammonia concentration can be measured in venous blood, by using an ammonia specific electrode according to the method of H. F. Proelss, et al., *Clin. Chem.* 19: 1162–1169 (1973), incorporated herein by reference. In order to minimize liberation of bound ammonia by hydrolytic processes the blood samples will be cooled immediately to 0° C. and deproteinized by mixing with an equal volume of 0.4M perchloric acid. After dilution 1:1 of the mixture with 0.2M perchloric acid, the proteins will be removed by centrifugation. Ammonia concentrations in the clear supernatants will be determined as follows: 0.5 ml aliquots will be mixed at room temperature with 20 μl 10M sodium hydroxide. An ammonium specific electrode (such as one obtainable from Orion Research Inc., Cambridge, Mass.) will be inserted into the mixture and the voltage generated by ammonia will be determined. Solutions with known concentrations of ammonium chloride will be used for calibration of the ammonia specific electrode.

EXAMPLE 3

The activity of the compounds of this invention to prevent or reduce the accumulation of β-amyloid plaques and thus the usefulness in the treatment of senile dementia of the Alzheimer's type and other conditions known to be associated with the formation of β-amyloid plaque such as Down's syndrome can be demonstrated by various in vitro and in vivo models of β-amyloid plaque formation. For example the ability of the compounds of this invention to prevent or reduce the accumulation of β-amyloid depositions can be demonstrated by several cellular and cell free in vitro methods described as Assay's 1–3 as follows. These assays make use of the fact that native β-APP is expressed by cells and is processed to produce 11–12 KDa C-terminal fragments and β-amyloid. The endogenous level of β-APP expression can be enhanced if desired by transfecting β-APP cDNA sequences, e.g., β-APP (751) into the cells using standard methodology.

IN VITRO ASSAYS

Assay #1: immunoprecipitation

Cells: CHO-K1 (Chinese Hamster Ovary; ATCC origin) cell line stably transfected to express large amounts of βAPP-695, and referred to as "CP-6-36" are used for screening of β-APP depositions. Other mammalian cultured cell lines can also be used and have been used. For example, the human neuronal cell line SK-N-ML (ATCC origin) gives good results under the same assay conditions. Transfection with βAPP-695 is not a requisite of 8A4 production; it merely enhances the βA4 signal. In preparation for an experiment, CP-6-36 cells are seeded at low density in 10 cm dishes and grown for two to four days to a confluent monolayer (~$1.5\times10^7$ cells per dish) in a 37° C. /5 $CO_2$ incubator; growth media consists of DMEM 21/Coon's F12 (1:1)+10% FBS (fetal bovine serum) +50 U/mL penicillin and 50 μg/mL streptomycin.

Treatment: All compounds are initially screened on CP-6-36 cells at a dose of 200 μM. Prior to testing, a 20 mM stock of each compound to be tested is prepared using cell culture grade DMSO as a solvent. Each 20 mM stock compound is then diluted 100-fold into serum free EMEM media deficient in the amino acids cysteine and methionine ("Cys-/Met- EMEM"), giving a 200 μM final concentration of compound in the media. To begin the experiment the cells are "starved" for cysteine and methionine by washing the cell monolayers 3 times with 3 mL/dish of Cys-/Met- EMEM, then incubating (37° C./5% $CO_2$) with 3 mL/dish of the same media for 15 minutes. This media is aspirated from the dishes, then media containing the compounds at 200 μM is added at 3 mL/dish. These plates and a "control" dish (3 mL/dish Cyst-/Met- EMEM containing 1% DMSO and no compound) are incubated as above for 15 minutes. This media is aspirated, then to each dish an additional 3 mL of the media from the previous step now containing $^{35}$S-Trans label ($^{35}$-S labeled cysteine and methionine) at ~150 μCi/mL is added. The cells are incubated as above for 4 hours.

Harvest: At the end of the 4 hour labeling period, the cells are observed under the microscope for overall appearance and to check for gross toxicity effects of the compounds, after which the dishes of cells are placed on ice. The conditioned media from each dish is transferred to 15 mL conical screw-cap tubes, centrifuged at 2000 rpm for 10 minutes and transferred to a set of similar tubes, leaving behind any pelleted cells. The labeled cell monolayers are washed three times with 2 mL/dish phosphate-buffered saline (PBS), then 1 mL of a buffer which promotes cell lysis (5% Triton X-114; 20 mM Tris, pH 7.5; 300 mM NaCl; protease inhibitors) is added to each dish, followed by a 10 minute incubation on ice. The cell lysates are scraped from the dishes and transferred to 1.5 mL microfuges tubes. The lysates are then sonicated for 4 minutes on ice, spun at high speed in a microfuge for 10 minutes, then transferred to 15 mL conical screw-cap tubes, leaving behind the pellet of cell debris.

Immunoprecipitation: In preparation for immunoprecipitation, the lysates harvested above are diluted in 5 mL of 1×RIPA buffer (10 mM Tris, pH 8.0; 150 mM NaCl; 0.125% $NAN_3$; 1% Triton X-100; 1% deoxycholate; 0.1 SDS); the conditioned media samples are immunoprecipitated without dilution. Both conditioned media and lysates are first precleared by adding 5 μL of normal rabbit serum to each sample, rocking 10 minutes at room temperature, followed by the addition of 100 μL 10% protein A-Sepharose (PAS) in RIPA buffer, and rocking at room temperature for 1.5 hours. The samples are then centrifuged at 3000 rpm, and the supernatants are transferred to new 15 mL tubes. The precleared lysates are then immunoprecipitated by adding 30 μL of an antibody which recognizes the carboxyl terminus of βAPP to each tube, rocking for 10 minutes at room temperature, followed by the addition of 100 μL of 10% PAS and rocking at room temperature for 1.5 hours. The precleared conditioned media samples are immunoprecipitated identically, however 45 μL of an antibody which recognizes βA4 is used instead of the carboxyl terminal directed antibody. All samples are then centrifuged for 1 minute at 3000 rpm to pellet the PAS-antibody complexes, and the resulting pellets are washed extensively; 4 times with a high salt buffer (50 mM Tris, pH 7.5; 500 mM NaCl; 5 mM EDTA; 0.5% Nonidet P-40), 3 times with a low salt buffer (50 mM Tris, pH 7.5; 150 mM NaCl; 5 mM EDTA; 0.5 Nonidet P-40), and 2 times with 10 mM Tris buffer, pH 7.5.

Gel electrophoresis: The washed pellets are boiled for 5 minutes in 50 μL of 2×Laemmli gel loading buffer. These samples as well as molecular weight markers are loaded onto a 16.5% SDS-polyacrylamide gel with Tris/Tricine reservoir buffers. The gel is run at 90 V for ~18–20 hours, fixed in 20% methanol/20% acetic acid, and dried onto filter paper at 65° C. for 2 hours. Autoradiography is used to visualize the results.

Analysis: Results are obtained by analysis of the autoradiogram. A positive acting compound is one which inhibits the 4 kDa μA4 protein band relative to the control sample, and which increases levels of the 9–12 kDa C-terminal protein bands relative to the control sample. Quantitation of inhibition of βA4 or increase of C-terminal bands can be made by densitometric scanning of the bands, normalized to control bands. A negative acting compound is one which shows no change in the yield of 4 kDa βA4 or 9–12 kDa C-terminal protein bands, relative to the bands from the control sample.

Additional testing: If a compound is to be found to be active (i.e., substantial inhibition of 4 kDa βA4 formation with concomitant increase in C-terminal fragments, by gel analysis), then a dose response experiment is performed to determine the lowest dose of compound necessary to elicit above effects. The dose range typically used is 12.5–300 μM, and with the exception of these dose changes, the experiment is done identically as described above. If a compound is found to be only slightly active or not active at all, the experiment is repeated using a higher dose, typically 400 μM. If a compound is found to be toxic (i.e., cells appear unhealthy by observation under the microscope, or lysates appear to not have been labeled well after gel analysis), then the compound is tested again at lower doses, for example: 25, 50 and 100 μM, to determine the effect of the compound at a non-toxic dose.

Assay #2: Radioimmunoassay

Preparation and Sepak concentration of media for the RIA: Cultured mammalian cells such as Chinese hamster ovary (CHO) cells or human neuronal SK-N-ML cells produce β-amyloid and secrete this peptide into the culture medium. If cells are treated with potential inhibitors of β-amyloid formation, no soluble β-amyloid would be found in the medium of the treated cells. As with Assay #1, varying doses of inhibitory compounds can be tested beginning with 200 μM. For CHO cells, both wild type and β-APP695 transfected, 10 cm plates are incubated in 2 mL EMEM (serum free) for 4 to 6 hours at 37° C. in the presence or absence of inhibitory compounds to be evaluated. The medium is removed and centrifuged for 10 minutes at 1500 rpm (Sorvall RT6000B) to remove any cells/debris. The medium is either used immediately or stored at −20° C.

The Sepak C18 step is performed to remove salts and other unwanted contaminants and to concentrate the β-amyloid peptides. Medium sample (2 ml) is passed through a C18 Sepak cartridge and the cartridge is washed in 2 ml 5% $CH_3CN$ in 0.1% TFA. The runthrough and the 5% $CH_3CN$ wash are discarded. The cartridge is eluted with 2 mL 25% $CH_3CN$ in 0.1% TFA followed by 2 mL elution in 50% $CH_3CN$ in 0.1% TFA. Both elutions are collected and dried in the speedvac and taken up in 125 μL to 250 μL of 10% isopropanol in water for assaying in the RIA. The 25% $CH_3CN$ fraction contains most of the phenol red from the media but no β-amyloid peptide. The 50% $CH_3CN$ fraction contains the β-amyloid peptides.

Preparation and HPLC purification of $^{125}I$ labeled β-amyloid 1–40: Synthetic β-amyloid 1–40 (10 μg) is labeled with $^{125}I$ (1 mCi) by the Chloramine T method. The reaction is carried out at room temperature. In an Eppendorf tube, 10 μL of $^{125}I$ (1 mCi in NAOH solution) is added to 10 μL of β-amyloid 1–40 (1 mg/mL in 20% Isopropanol) and 80 μL 0.1M NaPhosphate, pH 7.4 and mixed. The reaction is initiated by adding 30 μL Chloramine-T (1 mg/mL, in 0.1M NaPhosphate, pH 7.4) mixing and incubating 1 minute. The reaction is stopped by adding 150 μL NaMetabisulfite (2mg/mL, 0.1M NaPhosphate, pH 7.4).

The reaction mixture (280 μL) is diluted with equal volume of water and run on a Sepak C18 cartridge to separate the labeled peptide. The Sepak is washed twice in 5% $CH_3CN$ (1 mL each) and eluted three times in 50% $CH_3CN$ (1 mL each) and washed again twice in 95% $CH_3CN$ (1 mL each). Almost all of the labeled peptide elutes in the first 50% $CH_3CN$ elution. This elution is stored at −70° C. and purified by HPLC as needed for the RIA.

The labeled peptide is purified by reverse phase HPLC on a C8 cartridge (4.6 mm×3 cm, Brownlee). The column is run in a linear gradient from 5% to 45% $CH_3CN$ in 0.1% TFA in 30 minutes at a flow rate of 0.5 ml/min. Fractions (0.5 mL) are collected and counted. The peak fraction containing the labeled peptide is stored at −20° C. and used within 3 days in the RIA.

Radioimmunoassay: The buffers used in the RIA are 1) RIA buffer: 0.1M NaPhosphate, pH 7.4 containing 0.1% BSA and 0.1% Triton-X-100.2) Sample buffer: 10% Isopropanol in water. 3) Tracer buffer: 0.2M NaPhosphate, pH 7.4 containing 0.1% BSA in 0.1% Triton-X-100.The β-amyloid specific antibodies are used at dilutions where approximately 30% of the labeled peptide is bound in the absence of competing ligand. The dilutions of the antibodies are prepared in RIA buffer. The antibodies used in the RIA include three different sera raised to human β-amyloid 1–40 synthetic peptide (BA#1, BA#2, and 6514). BA#1 is used at final dilution of 1/900, BA#2 at 1/1600 and 6514 at 1/2500. The HPLC purified labeled peptide is diluted in tracer buffer to give between 7000 and 9000 cpm in 50 μL. Total displacement is done in the presence of high concentration (2.5 μM) of β-amyloid 1–40. The β-amyloid 1–40 standards are prepared in sample buffer. The assay volume is 200 μL. Components are added in the following order:

100 μL Ab in RIA buffer

50 μL Unknown sample or standard or TD in sample buffer

50 μL Labeled peptide (7000–9000 cpm in tracer buffer)

The samples are mixed and incubated overnight at 4° C. To separate the bound counts from the free counts, the assay is terminated with polyethylene glycol (PEG). To each assay tube, 50 μL of normal rabbit serum is added, followed by 800 μL of PEG (MW6000–8000, 15.8% in RIA buffer). The samples are incubated for 10 minutes at 4° C. and centrifuged 3200 rpm, 20 minutes (Sorvall, RT600B). The supernatant is aspirated and the pellets are counted in the gamma counter.

Analysis: Results from antibody binding are interpreted based on displacement of the labeled β-amyloid tracer. A positive result is one in which no displacement of tracer is observed, i.e., medium does not contain secreted β-amyloid indicating the compound tested is effective in inhibiting β-amyloid production. A negative result is one in which displacement of tracer for antibody binding is seen and equivalent to untreated control cells.

An enzyme linked immunosandwich assay (ELISA) can also be employed to identify active compounds. Cultured mammalian cells (such as CHO CP-6 or SK-N-MC) producing β-amyloid protein are prepared and treated with compounds as described for Assay #1 except that radiolabelling of cell protein is eliminated. Conditioned media from treated cell cultures is harvested and clarified of cellular debris by low-speed centrifugation. The conditioned media is then assayed in a 96 well ELISA format utilizing β-amyloid-specific antibodies. One β-amyloid antibody serves as the capture reagent for the β-amyloid present in the media samples, the second β-amyloid-specific antibody which recognizes a different epitope on the β-amyloid protein serves as a component of the detector complex. The second β-amyloid antibody is conjugated with biotin which can be detected by strept-avidin. A third antibody which is coupled to horseradish peroxidase is used to detect the β-amyloid:antibody; strept-avidin complex. Addition of o-phenylenediamine substrate plus $H_2O_2$ and citrate phosphate pH 5 allows for peroxidase activity which is quantitated by reading the colorimetric change in the mixture at $OD^{490}$nm. Typically, serial three-fold dilutions of each medium sample is made in the 96 well plate in addition to a standard, synthetic β-amyloid 1–40 protein. A positive result is one in which little or no reactivity, i.e., adsorbance at $OD^{490}$nm, is obtained indicated the absence of β-amyloid protein in the medium sample as a result of inhibition by the compound tested. Partially active inhibitors would give some but not equivalent absorbance at $OD^{490nm}$ to a control medium sample from untreated cells. Precise quantitation can be achieved by comparing sample values to the standard.

IN VIVO ASSAYS

The activity of the compounds of this invention to prevent or reduce the accumulation of β-amyloid plaques can be demonstrated in an transgenic mouse model of β-amyloid plaque accumulation and in a dog model using dogs with a natural, genetic predisposition to the formation of β-amyloid plaque. Transgenic mice which overexpress human β-APP (751) or β-APP (770) in neuronal cells and display histopathology associated with Alzheimer's disease are described, for example, in PCT/US91/04447. In such animal models, the reduction of histopathology and/or symptoms associated with β-amyloid depositions such as memory loss, can be used to demonstrate the ability of the compounds to treat the therapeutic conditions resulting from β-amyloid plaque formation such as Alzheimer's Disease and the memory impairment associated with Down's syndrome.

Since the histopathology in the transgenic mice is more frequent with increased age of the animal, 2 month old mice would be desirable. The 2 month animals would have minimal pathology which would increase with time in the absence of inhibitory drug. All animals in the experiment would be from a single pure bred pedigree. One group of mice (n=12) would receive vehicle only; a second group (n=12) would receive a low dose of drug; a third group (n=12) a moderate dose; and a fourth group (n=12) a high dose. Dosage would be determined from the above assays taking into account body weight, compound half-life, etc. Ideally, mice would be treated for several months. Delivery of the compound could be by injection, oral route, an implant with timed release, etc., as dictated by the compound profile. Evaluation of treatment would be made using immuno-histochemistry to determine the frequency of β-amyloid immunoreactive deposits in coronal midline sections of brain scored by an investigator blinded from the experimental treatment. Another marker of pathology, Alz50 immunoreactivity, would also be scored for frequency of occurrence using the same number of brain tissue sections from all mice in the study. A positive result of drug action would be the absence or reduced frequency of both pathological markers. A physiological and/or behavioral correlate unique to the β-amyloid transgenic mice can also be used to demonstrate drug action.

Some canine races have been reported to have β-amyloid accumulations (Giaccone et al., *Neuroscience Letters* Vol.114, pp 178–183 (1990)). Aged non-human primates display β-amyloid pathology, as well as memory impairments (Cork et al., *American Journal of Pathology*, Vol .137, pp 1383–1392 (1990)); Podlisny et al., *American Journal of Pathology* Vol.138, pp 1423–1425 (1991)). Tests with canines and non-human primates would most likely follow a somewhat different experimental design with drug application time being longer.

EXAMPLE 4

In order to test the efficacy of treatment using the compounds of the present invention on the cognitive and non-cognitive behavioral dysfunctions in DAT patients, the ADAS (Alzheimer's Disease Assessment Scale) can be used according to the method of W. G. Rosen, et al., *Am. J. Psychiatry* 141: 1356–1364 (1984), incorporated herein by reference. Cognitive functioning can be assessed on 17 items. These include memory functions, language functions and ideational praxis task and constructional praxis. Non-cognitive behaviors will be rated on 23 items which include mood state (depression, anxiety), vegetative symptoms, socialization skills, cooperation, initiative for activities of daily living, psychotic symptoms, motor activity, agitation, concentration and nocturnal confusion.

EXAMPLE 5

This example describes procedures useful in determining other agents useful in combination therapy with the compounds of the present invention and for use alone.

Materials and Methods:

Chemicals: Usual laboratory chemicals were obtained from Baker Chemical (Derenter, The Netherlands) or Merck (Darmstadt, Germany). L-Carnitine, L-acetylcarnitine, N-acetyl-L-glutamate and the amino acids L-ornithine, L-arginine and L-citrulline were from Sigma Chemical Co. (St. Louis, Mo.). 5-Fluoromethylornithine.2HCl.$H_2O$ (5FMOrn) is a compound of the present invention. [(+)-5-Methyl-10,11-dihydro-5H-dibenzo[a,d]cycloheptene-5,10-imine) was from Bioblock Scientific (Illkirch, France). (R)-4-oxo-5-phosphono-norvaline (Whitten et al., *J. Med. Chem.* (1990) 11:2961–2963, is a product of Marion Merrell Dow Inc.

Laboratory animals: Female CDl mice (Charles River, St. Aubin-les-Elbeuf, France) were kept in groups of 10 under standardized conditions (water and standard rodent chow ad libitum, 22° C., 60% relative humidity, 12 hours light, 12 hours dark cycle).

Drug regimen and intoxication with ammonium acetate: Mice are pretreated by i.p. administration of 5-fluoromethylornithine, usually 16 hours before the i.p. injection of 13 or 15 mmol.kg$^{-1}$ ammonium acetate (1.00 g, respectively 1.15 g in 10 ml of water; 0.1 ml per 10 g body weight). Amino acids and the other compounds are given subcutaneously (s.c.) usually 1 hour before intoxication with ammonium acetate. (Treatments different from these are mentioned in the legends of Tables.)

After intoxication with ammonium acetate the appearance of clonic seizures, the loss of the righting reflex, coma, and tonic hind limb extensions are recorded. Survivors exhibit normal behavior 2 hours after intoxication.

Tissue preparation: Mice are decapitated and brains rapidly (<10 seconds) isolated, frozen in liquid nitrogen, and stored at −80° C. until analysis. For the determination of ammonia, glutamine and glutamate the frozen brains are homogenized in 10 volumes of ice-cold 0.2M perchloric acid. After 1 hour at 2° C. the homogenates were centrifuged, and the supernatants submitted to the assay procedures on the same day, in order to minimize hydrolysis of glutamine or of other hydrolytically releasable forms of ammonia.

Amino Acid and ammonia: For the determination of glutamine and glutamate aliquots of the perchloric acid, brain extracts are separated by using the isocratic elution mode of a previously published reversed-phase HPLC method (Seiler and Knödgen, 1985). For ammonia determinations, an ammonia selective electrode (Orion Research Inc., Cambridge, U.S.A.) is used. Standard solutions of ammonium chloride are prepared for the establishment of a calibration curve for each series of samples. (For details, see Seiler et al., 1992.)

TABLE 1

Protection of mice against intoxication with 13 mmol · kg$^{-1}$ (i.p.) ammonium acetate by amino acids and related compounds alone and in combination with 5 μmol · kg$^{-1}$ 5-fluoromethylornithine (5FMorn)

| Drug | Dose mmol · kg$^{-1}$ | with loss of righting reflex | Percent animals with tonic seizure | Percent survivors |
|---|---|---|---|---|
| A. Single drug treatment | | | | |
| Vehicle (3% $NaHCO_3$) | — | 100 | 100 | 0 |
| L-Ornithine | 10 | 90 | 20 | 90 |
| L-Arginine | 10 | 80 | 10 | 90 |
| L-Citrulline | 5 | 70 | 10 | 100 |
| | 3 | 70 | 10 | 90 |
| | 0.75 | 90 | 70 | 40 |
| N-Acetyl-L-glutamate | 5 | 100 | 90 | 10 |
| L-Carnitine | 15 | 90 | 90 | 10 |
| L-Acetylcarnitine | 15 | 100 | 70 | 30 |
| B. Combined treatment with 5 μmol · kg$^{-1}$ 5FMorn | | | | |
| Physiol. saline | — | 60 | 60 | 40* |
| L-Citrulline | 0.75 | 90 | 30 | 80* |

TABLE 1-continued

Protection of mice against intoxication with 13 mmol · kg⁻¹ (i.p.) ammonium acetate by amino acids and related compounds alone and in combination with 5 μmol · kg⁻¹ 5-fluoromethylornithine (5FMorn)

| Drug | Dose mmol · $kg^{-1}$ | with loss of righting reflex | Percent animals with tonic seizure | Percent survivors |
|---|---|---|---|---|
| N-Acetyl-L-glutamate | 5 | 90 | 40 | 20 |
| L-Carnitine | 15 | 100 | 50 | 60* |
| L-Acetylcarnitine | 15 | 90 | 40 | 100* |

Groups of 10 CDl mice (female, weighing 22±3 g received either 5 μmol.$kg^{-1}$ 5FMOrn (i.p.) or physiol. saline. 15 hours later the above-mentioned drugs dissolved in 3% $NaHCO_3$ were administered subcutaneously, and another hour later 13 mmol.$kg^{-1}$ ammonium acetate (in water) was injected i.p.

The asterisk (*) indicates a statistically significant difference (p≦0.05) between single drug and combination treatment; (Non-parametric statistics (Siegel, 1956).)

TABLE 2

Intoxication of mice with 15 mmol · $kg^{-1}$ (i.p.) ammononium acetate. Effects of pretreatment with 0.1 mmol · $kg^{-1}$ 5-fluoromethylornithine (5FMorn) and other compounds known to antagonize acute ammonia intoxication

| Treatment | Percent animals with tonic seizure prior to the loss of righting reflex | with tonic seizure after the loss of righting reflex | with loss of righting reflex without tonic seizure | survivors |
|---|---|---|---|---|
| None | 100 | 0 | 0 | 0 |
| 5FMorn | 35 (20–50)[a] | 63 (50–80)[a] | 2 (0–10)[a] | 2 (0–10)[a] |
| L-Citrulline (5 mmol · $kg^{-1}$) | 70 | 30 | 0 | 0 |
| 5FMorn + L-Citrulline | 30 | 70 | 0 | 0 |
| L-Ornithine (10 mmol · $kg^{-1}$) | 0 | 100 | 0 | 10 |
| 5FMorn + L-Ornithine | 0 | 80 | 20 | 20 |
| L-Arginine (10 mmol · $kg^{-1}$) | 40 | 60 | 0 | 0 |
| 5FMorn + L-Arginine | 30 | 70 | 0 | 0 |
| L-Carnitine (15 mmol · $kg^{-1}$) | 100 | 0 | 0 | 0 |
| 5FMorn + L-Carnitine | 0 | 60 | 40 | 60* |
| L-Acetylcarnitine (15 mmol · $kg^{-1}$) | 0 | 100 | 0 | 0 |
| 5FMorn + L-Acetylcarnitine | 0 | 50 | 50 | 60* |
| N-Acetyl-L-glutamate (5 mmol · $kg^{-1}$) | 30 | 70 | 0 | 0 |
| 5FMOrn + N-Acetyl-L-glutamate | 30 | 70 | 0 | 0 |

[a]Mean value of four independent experiments; range in parentheses.

Each group consisted of 10 female CDl mice (weighing 20±2 g). Pretreatment with 0.1 mmol.$kg^{-1}$ (i.p.) 5FMOrn 16 hours before 15 mmol.$kg^{-1}$ ammonium acetate administration (i.p.). Amino acids and related compounds were given s.c. 1 hour before ammonium acetate.

The asterisk (*) indicates a statistically significant (p=0.05) difference between groups treated with a single drug and the combination with 5FMOrn; non-parametric statistics (Siegel, 1956).

Ammonium acetate, 5FMOrn and ornithine, arginine, and citrulline were dissolved in water; carnitine, acetylcarnitine and N-acetylglutamate in 2% $NaHCO_3$ (0.1 ml per 10 g body weight).

TABLE 3

Ammonia, glutamine and glutamate in the brain of mice, 10 min after administration of ammonium acetate. Effect of pretreatment with 5-fluoromethylornithine (5FMOrn) and other compounds known to antagonize acute ammonia intoxication

| Treatment | Ammonia | Glutamine μmol | Glutamate per g | Glutamine / Glutamate |
|---|---|---|---|---|
| None[a] | 0.9 ± 0.1 | 5.9 ± 0.4 | 12.6 ± 0.3 | 0.47 ± 0.03 |
| Ammonium acetate | 2.7 ± 0.5 | 10.3 ± 0.8 | 10.5 ± 0.4 | 0.98 ± 0.09 |
| 5FMOrn (0.1 mmol · $kg^{-1}$) | 1.5 ± 0.2* | 8.9 ± 0.7 | 10.8 ± 0.5 | 0.82 ± 0.05 |
| Ornithine (10 mmol · $kg^{-1}$) | 1.5 ± 0.4* | 8.8 ± 0.5* | 11.5 ± 0.5 | 0.77 ± 0.03* |
| Ornithine + 5FMOrn | 1.3 ± 0.2* | 8.7 ± 0.2* | 11.3 ± 0.2 | 0.77 ± 0.03 |

TABLE 3-continued

Ammonia, glutamine and glutamate in the brain of mice, 10 min after administration of ammonium acetate. Effect of pretreatment with 5-fluoromethylornithine (5FMOrn) and other compounds known to antagonize acute ammonia intoxication

| Treatment | Ammonia | Glutamine μmol | Glutamate per g | Glutamine / Glutamate |
|---|---|---|---|---|
| Arginine (10 mmol · $kg^{-1}$) | 1.5 ± 0.2* | 8.9 ± 0.3* | 10.2 ± 1.0 | 0.89 ± 0.07 |
| Arginine + 5FMOrn | 1.8 ± 0.3* | 8.4 ± 0.9* | 10.2 ± 0.9 | 0.82 ± 0.04 |
| Citrulline (5 mmol · $kg^{-1}$) | 1.6 ± 0.5* | 7.3 ± 0.4* | 11.9 ± 0.5 | 0.61 ± 0.04 |
| Citrulline + 5FMOrn | 1.3 ± 0.2* | 7.0 ± 0.4* | 11.6 ± 0.4 | 0.60 ± 0.02* |
| N-Acetylglutamate (5 mmol · $kg^{-1}$) | 1.8 ± 0.5* | 9.2 ± 0.9 | 11.3 ± 0.5* | 0.81 ± 0.08 |
| N-Acetylglutamate + 5FMOrn | 1.2 ± 0.1** | 8.2 ± 0.3** | 11.9 ± 0.4 | 0.69 ± 0.04** |
| L-Carnitine (15 mmol · $kg^{-1}$) | 1.7 ± 0.5* | 8.8 ± 0.4* | 11.4 ± 0.3* | 0.77 ± 0.06 |
| L-Carnitine + 5FMOrn | 1.2 ± 0.2** | 7.8 ± 0.7** | 11.9 ± 0.3 | 0.65 ± 0.04 |
| L-Acetylcarnitine (15 mmol · $kg^{-1}$) | 2.5 ± 0.3 | 8.9 ± 0.6 | 11.4 ± 0.4* | 0.78 ± 0.04 |
| L-Acetylcarnitine + 5FMOrn | 1.4 ± 0.3** | 7.8 ± 0.4** | 11.5 ± 0.8* | 0.67 ± 0.03** |

5-Fluoromethylornithine (0.1 mmol · $kg^{-1}$) was given i.p. 16 hours before 8 mmol · kg ammonium acetate (i.p.). Amino acids and related compounds were administered subcutaneously 1 hour before ammonium acetate. The animals were killed by decapitation 10 minutes after administration of ammonium acetate.

[a]With the exception of these animals, all other groups received 8 mmol · $kg^{-1}$ ammonium acetate.

*Statistically significant difference ($p \leqq 0.05$) between ammonium acetate treated "controls" and groups receiving pretreatment with a drug.

**Statistically significant difference ($p \leqq 0.05$) between groups receiving a single drug, and the drug combination with 5FMOrn (Student's t-test).

For pharmacological end-use applications, the compounds of Formula I are preferentially administered in the form of their pharmaceutically acceptable acid addition salts. Of course, the effective dosage of the compounds will vary according to the individual potency of each compound employed, the severity and nature of the disease being treated and the particular subject being treated. In general, effective results can be achieved by administering a compound at a dosage of about 0.01 mg to about 20 mg per kilogram of body weight per day of the compounds of formula I administered systemically. Therapy should be initiated at lower dosages. The dosage thereafter may be administered orally in solid dosage forms, e.g., capsules, tablets, or powders, or in liquid forms, e.g., solutions or suspensions. The compounds may also be injected parenterally in the form of sterile solutions or suspensions. For combination therapy, therapeutic agents administered concurrently or consecutively to administration with compounds of Formula I are administered preferably in a dosage of about 0.1 mg to about 100 mg per kilogram of body weight per day.

In practicing the method of this invention, the compounds of formula I and/or the therapeutic agents in combination therapy are preferably incorporated in a composition comprising a pharmaceutical carrier and from about 5 to about 90 percent by weight of a compound of the invention or a pharmaceutically acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired.

The preferred route of administration is oral administration. For oral administration the active compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptable surfactant, suspending agent, or emulsifying agent.

The active compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as polyethylene glycol 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically acceptable adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylene-polypropylene copolymers; and amphoteric detergents, for example, alkyl beta-aminopropionates, and 2-alkylimidazoline quarternary ammonium salts, as well as mixtures. The parenteral compositions of this invention will typically contain from about 0.5 to about 25% by weight of the formula I compound in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of the present invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

What is claimed is:

1. A process of making (2S,5S)-5-fluoromethylornithine comprising:

adding a sufficient amount of wet penicillin acylase to a solution of (2R,5R) and (2S,5S)-6-fluoromethyl-3-(phenylacetyl)-amino-2-piperidone;

recovering ((2S,5S)-6-fluoromethyl-3-amino-2-piperidone from the solution; and adding a sufficient amount of an acid to produce (2S,5S)-5-fluoromethylornithine.

* * * * *